United States Patent [19]

Gambert et al.

[11] Patent Number: 5,064,769
[45] Date of Patent: Nov. 12, 1991

[54] IMMUNOASSAY OF APOLIPOPROTEIN-B OF LOW DENSITY LIPOPROTEINS IN PLASMA

[75] Inventors: Philippe Gambert; Emmanuel Louvrier, both of Dijon, France

[73] Assignee: Société à Responsabilité Limitée dite: Spiral, Dijon, France

[21] Appl. No.: 829,206

[22] Filed: Feb. 14, 1986

Related U.S. Application Data

[63] Continuation of Ser. No. 543,062, Oct. 18, 1983, abandoned.

[51] Int. Cl.$^5$ .................. G01N 33/561; G01N 33/53; C12Q 1/00; C25B 1/00
[52] U.S. Cl. ...................... 436/516; 436/71; 436/316; 436/811; 435/7.1; 204/182.8; 204/299 R
[58] Field of Search .................. 436/71, 516, 811; 204/182.8, 299 R; 435/7.1

[56] References Cited

U.S. PATENT DOCUMENTS 3,930,983  1/1975  Sieber .

OTHER PUBLICATIONS

Kistner, G. M. et al., Atherosclerosis 38 (1981) pp. 57–61.
Krauss, R. M. et al., J. Lipid Res. 23 (1982) pp. 97–104.
Sniderman, A. et al., Proc. Natl. Acad. Sci. U.S.A. 77 (1980) pp. 604–608.
Kwapinski, G., The Methodology of Investigative and Clinical Immunology, R. E. Krieger Pub. Co., Fla., 1982, p. 56.
Chemical Abstracts, vol. 93, No. 1, Issued Jul. 1, 1980, p. 317, #3248t, Heuck, C. C., "Methodological Aspects . . . Immonoeketrophoresis".

*Primary Examiner*—Robert A. Wax
*Assistant Examiner*—David R. Preston
*Attorney, Agent, or Firm*—Foley & Lardner

[57] ABSTRACT

Method of assaying the apolipoprotein B (apo B) of low density lipoproteins (LDL) in serum enabling the performance successively, in a single operation, of separation of the LDLs from other lipoproteins containing apo-B by electrophoresis in a polyacrylamide gel having a controlled degree of cross-linking and assay of the apo-B of the LDLs thus separated by electro-immunodiffusion in an agarose gel containing anti-apo B. Samples are placed in wells formed in the acrylamide gel, and the height of the precipitation arcs in the agarose gel is measured.

13 Claims, 1 Drawing Sheet

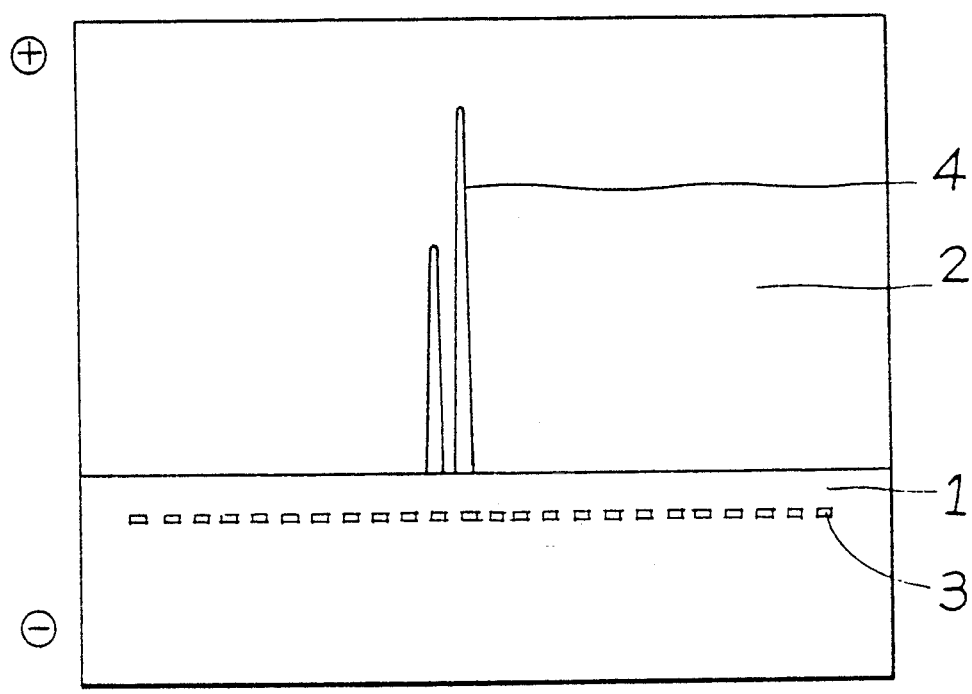

IMMUNOASSAY OF APOLIPOPROTEIN-B OF LOW DENSITY LIPOPROTEINS IN PLASMA

This is a continuation of application Ser. No. 543,062, filed Oct. 18, 1983 now abandoned.

BACKGROUND OF THE INVENTION

This invention relates to a method enabling the immunoassay of a single protein species in a family of proteins or of proteinic complexes having a common antigen determinant but of different sizes.

The method according to the invention enables the successive performance, in a single operation using a novel electrophoretic system of a separation of the proteins according to their size in a controlled cross-linked medium, and an assay by electroimmunodiffusion according to the method of Laurell, C. B. Anal. Biochem. 15 45–52 (1966). The controlled cross-linked medium in which prior electrophoretic migration is carried out enables the blocking of the proteins of size greater than that of the protein to be assayed, so that these proteins cannot interfere in the subsequent assay by electroimmunodiffusion.

It is a particular object of the invention to provide a method of assay of apolipoprotein B (denoted below apo-B) occurring in low density lipoproteins (denoted below LDL) in the serum.

The apolipoprotein-B (apo B) is a constituent protein of different serum lipoprotein complexes: the very low density lipoproteins (VLDL), the intermediate density lipoproteins (IDL) and the low density lipoproteins (LDL). The sizes, chemical compositions, structures and physiopathological roles of these complexes are very different.

Goldstein J. L. and Brown M. S., Ann. Rev. Biochem. 46 897–930 (1977) have shown that apo B of LDL regulates the cell metabolism of the seric lipoproteins and have suggested that it would play a key role in the occurence of the atherosclerotic process. Recent clinical studies (Sniderman A, et al., Proc. Nat. Acad. Sci. U.S.A. 77 604–608 (1980) have confirmed these experimental data by showing the discriminating character of the serum concentration of apo B of the LDLs in the diagnosis and the prognosis of coronopathies.

It is to be noted in addition that the LDLs form a heterogeneous molecular family in which it is possible to individualize several fractions (Krauss R. M. and Burke D. J. J. Lipid. Res. 23 97–104 (1982)) and particularly the lipoprotein lpa of particular constitution and of which the responsibility in the early development of atherosclerosis has been suspected (Kostner G. M. et al. Atherosclerosis 38 51–61 (1981)).

The assay methods of apo B at present proposed all determine the total serum apo B without differentiating the apo B according to its origin and hence its physiological significance. Determination of apo B of different lipoprotein fractions has indeed been proposed by Sniderman et al. (cited above), but it involves the separation of the lipoproteins by preparative ultracentrifugation, a long, expensive and not really quantitative method.

SUMMARY OF THE INVENTION

It is an object of the method according to the invention to enable the assay of apo B of total LDLs without interference from other lipoproteins. A modification of the method enables the assay of the apo B connected to fraction Lpa to be eliminated.

According to the invention, under the action of an electrical field there are carried out successively, in a single operation:
separation by electrophoresis of the LDLs from the other lipoproteins containing the apo B,
determination of the apo B of the LDLs by electroimmunodiffusion according to the method of Laurell C. B. (cited above).

The first step of separation is carried out by electrophoretic migration of samples in a polyacrylamide gel or an equivalent polymer gel, cross-linking of which is such that there is passage of the IDLs and retention of the other lipoproteins containing apo B, in particular the VLDLs which all have a size greater than that of the LDLs. Hence the cross-linking of the gel is controlled in the course of its preparation so that the gel obtained blocks any standard protein of diameter greater than 30 nm.

The second step of determination is carried out by electrophoretic migration of the LDLs in an agarose gel containing anti-apo B antibodies.

The separative step takes into account the specificity of the assay. It also improves its accuracy and its linearity.

In fact, what limits the performance of the electroimmunodiffusion techniques is the existence, before any electrophoretic migration, of a passive diffusion of the samples in the agarose, a diffusion which is variable from one deposit to another, which has repercussions on the height of the precipitation ares of the immune complexes and which for this reason results in defects of reproducability and of linearity. It has been proposed to offset this drawback by forming the deposits while the plate is under voltage (Ayrault-Jarrier M. Ann. Biol. Clin. 40 187–194 (1982)), this technique is neither completely effective, nor compatible with the rules of safety. In the method according to the invention, the samples are deposited inside wells formed in the acrylamide gel which renders any diffusion impossible and eliminates the indicated defects caused by passive diffusion.

According to a modification of the method according to the invention, the apo B coupled to the lipoprotein Lpa is excluded from the assay by introducing an additional gel between the separation gel and the electroimmuno diffusion gel. This is an acrylamide gel containing specific antibodies to the lipoprotein Lpa. On migration of the LDLs in this gel, the lipoproteins Lpa form, with the corresponding antibodies, immune complexes of size such that their migration becomes impossible. Only the other LDLs continue their migration in the direction of the electroimmundoffusion.

The method according to the invention is practised by the employment of a novel analytical means composed of a support constituted for one part, by an acrylamide-agarose gel, for another part, by an agarose gel. The support used as a horizontal support for the electrophoretic migration, comprises: a) On the cathodic side, a first portion constituted by a polyacrylamide gel containing a low proportion of agarose having the purpose of ensuring the mechanical strength of the gel, and which can vary from 0.05 to 5 by weight of the gel.

For the preparation of this gel, there is used, in the course of polymerisation, conventional cross-linking agents, such as methylene-bis-acrylamide or di-allyl-tartar-diamide, so as to obtain a gel which does not allow the passage of standard proteins having a diameter greater than 30 nm.

If, for example, one starts with a mixture with 30 g/liter of acrylamide and 7 g/liter of agarose, the cross-linking agent is added in a proportion of 10% by weight with respect to the acrylamide. Wells intended for the deposition of the samples are formed in this first gel at a distance of some millimeters, 2 mm for example, from the interface of the two gels. b) On the anodic side, a second portion, constituted by an agarose gel (for example 10 g/l) containing anti-apo B antibodies.

In order to follow the migration and the precipitation of the lipoproteins, the samples are mixed volume by volume with a solution of Sudan Black (5 g/l in ethyleneglycol), a dye for lipids.

A microliter of each mixture is deposited in the well reserved for this purpose.

A potential difference of 100 V is maintained for 3 hours between the ends of the plate.

When the heights or the surfaces of the precipitation arcs of the immune complexes are measured. The concentrations of apo B in the samples are calculated by comparison with the heights obtained with preparations containing known concentrations of apo of LDLs.

DESCRIPTION OF A PREFERRED EMBODIMENT

The attached drawing represents an analytical element according to the invention, comprising a gel 1 ensuring the blocking of the VLDLs and a gel 2 containing the anti-apo B antiserum. The samples are deposited in the wells 3, and at 4 are seen the precipitation arcs of the immune complexes.

According to a modification of the method according to the invention, the lipoprotein Lpa is excluded from the assay:

Between the two gels previously described is deposited a third acrylamide-agarose gel (for example, acrylamide 30 g/l, agarose: 7 g/l) containing anti-Lpa antibodies.

The operational method is otherwise identical to that described above.

The method according to the invention enables the apo B of LDLs to be assayed with good reproducibility: c.v. less than 1% on the same support (n≃20). The linearity depends on the anti-apo B serum used in the electroimmunodiffusion gel. With an antiserum of commercial origin, the linearity extends from 0.3 to 1.8 g/l of apo B.

The assay method according to the invention also has good specificity: increasing overloads of VLDL of the serum to be assayed have not resulted in significant modifications of the peak heights.

The method described for the specific assay of the apo B of a single lipoprotein fraction may be applied to the assay of a single proteinic species in proteinic groups of which the constituents possess a common antigenic determinant, but are of different sizes.

We claim:

1. A method for determining the apolipoprotein B (apo B) of low density lipoproteins (LDL) directly in serum in which the LDLs are mixed with other lipoproteins containing apo B, said method comprising
    (1) first separating the LDLs from the serum by electrophoresis of said serum in a cathodic layer of polyacrylamide polymer gel having a controlled degree of cross-linking and pore size, so as to block the electrophoretic migration of any lipoprotein having a diameter greater than 30 nm in said gel layer, LDLs migrate through said gel layer and emerge from said gel layer, and then
    (2) determining the apolipoprotein B of the LDLs on their emergence from the cathodic layer, by immunoelectrophoresis in an anodic layer of agarose gel containing anti-apolipoprotein B antibodies (anti-apo B), an electric voltage being applied between the said cathodic layer and an end of said anodic layer so that the direction of migration is from said cathodic layer towards said anodic layer;
    wherein the polyacrylamide gel contains agarose in a proportion of from 0.05 to 5% by weight of the gel.

2. A method according to claim 1, wherein the polyacrylamide gel is obtained by cross-linking a 3% acrylamide solution in the presence of a cross-linking agent.

3. A method according to claim 2, wherein the acrylamide is cross-linked in the presence of cross-linking agent selected from the group consisting of methylene-bis-acrylamide and diallyl tartardiamide.

4. A method according to claim 1, wherein wells are formed in the polyacrylamide gel at a distance of at least 2 millimeters from the interface between the polyacrylamide gel layer and the agarose gel layer.

5. A method according to claim 1, wherein the agarose gel is 1% by weight agarose.

6. A method according to claim 1 wherein the voltage applied is 100 volts.

7. A method for determining the apolipoprotein B (apo B) of low density lipoproteins (LDL) directly in serum in which the LDLs are mixed with other lipoproteins containing apo B, said method comprising
    (1) first separating the LDLs from the serum by electrophoresis of said serum in a cathodic layer of polyacrylamide polymer gel having a controlled degree of cross-linking and pore size, so as to block the electrophoretic migration of any lipoprotein having a diameter greater than 30 nm in said gel layer, LDLs migrate through said gel layer and emerge from said gel layer, and then
    (2) determining the apolipoprotein B of the LDLs on their emergence from the cathodic layer, by immunoelectrophoresis in an anodic layer of agarose gel containing anti-apolipoprotein B antibodies (anti-apo B), an electric voltage being applied between the said cathodic layer and an end of said anodic layer so that the direction of migration is from said cathodic layer towards said anodic layer;
    wherein the migration of serum lipoprotein Lpa, is blocked by an intermediate polyacrylamide gel layer having said controlled degree of cross-linking and containing antilipoprotein Lpa antibodies, said intermediate layer being interposed between said polyacrylamide gel layer and said agarose gel layer.

8. An electrophoresis support for determining the apolipoprotein B of low density lipoproteins contained in serum, said support comprising
    a cathodic portion and an anodic portion disposed side by side, said cathodic portion comprising a layer of polyacrylamide polymer gel having a controlled degree of cross-linking and pore size so as to block the migration of any layer while low density lipoproteins migrate through said gel layer and emerge from said gel layer, and said anodic portion comprising a layer of agarose gel containing anti-apo lipoprotein B antibodies, and means for applying an electric voltage between the end of said cathodic portion and that of said anodic layer;

wherein an intermediate layer of polyacrylamide gel having said controlled degree of cross-linking and containing anti-lipoprotein Lpa antibodies is interposed between said polyacrylamide gel layer of said cathodic portion and the agarose gel layer of said anodic portion.

9. An electrophoresis support according to claim 2, wherein said polyacrylamide gel is obtained by crosslinking a 3% acrylamide solution in the presence of a cross-linking agent.

10. An electrophoresis support according to claim 9, wherein the acrylamide is cross-linked in the presence of a cross-linking agent selected from the group consisting of methylene-bis-acrylamide and diallyl tartardiamide.

11. An electrophoresis support according to claim 8, wherein said agarose gel is 1% by weight agarose.

12. An electrophoresis support according to claim 8, wherein wells are formed in the polymer gel at a distance of at least 2 millimeters from the interface between the polyacrylamide gel layer and the agarose gel layer.

13. An electrophoresis support for determining the apolipoprotein B of low density lipoproteins contained in serum, said support comprising a cathodic portion and an anodic portion disposed side by side, said cathodic portion comprising a layer of polyacrylamide polymer gel having a controlled degree of cross-linking and pore size so as to block the migration of any lipoprotein having a diameter greater than 30 nm in said gel layer while low density lipoproteins migrate through said gel layer and emerge from said gel layer, and said anodic portion comprising a layer of agarose gel containing anti-apo lipoprotein B antibodies, and means for applying an electric voltage between the end of said cathodic portion and that of said anodic layer;

wherein the polymer gel contains agarose in a proportion of from 0.05 to 5% by weight of the gel.

* * * * *